US009213784B2

(12) United States Patent
Thompson et al.

(10) Patent No.: US 9,213,784 B2
(45) Date of Patent: Dec. 15, 2015

(54) SYSTEM AND PROCESS FOR OPTIMIZATION OF DENTURES

(75) Inventors: Timothy C. Thompson, Fountain Hills, AZ (US); Scott C. Keating, Louisville, CO (US); Andrzej J. Jakson, Amherst, NY (US)

(73) Assignee: GLOBAL DENTAL SCIENCE LLC, Scottsdale, AZ (US)

( * ) Notice: Subject to any disclaimer, the term of this patent is extended or adjusted under 35 U.S.C. 154(b) by 372 days.

(21) Appl. No.: 13/823,662

(22) PCT Filed: Nov. 3, 2011

(86) PCT No.: PCT/US2011/059235
§ 371 (c)(1),
(2), (4) Date: Mar. 14, 2013

(87) PCT Pub. No.: WO2012/061655
PCT Pub. Date: May 10, 2012

(65) Prior Publication Data
US 2013/0218532 A1 Aug. 22, 2013

Related U.S. Application Data

(63) Continuation-in-part of application No. 12/939,141, filed on Nov. 3, 2010.

(51) Int. Cl.
*G06G 7/48* (2006.01)
*G06F 17/50* (2006.01)
(Continued)

(52) U.S. Cl.
CPC ............ *G06F 17/50* (2013.01); *A61C 13/0004* (2013.01); *G06T 17/00* (2013.01); *A61C 13/0024* (2013.01)

(58) Field of Classification Search
CPC ............ G06G 7/60; G06G 5/00; G06F 19/00; G06F 17/50; B32B 18/00; C04B 35/48; B65D 83/00; A61C 5/00; A61C 13/00; A61C 8/00; A61C 5/10; A61C 3/00; A61C 13/007
See application file for complete search history.

(56) References Cited

U.S. PATENT DOCUMENTS 200,445 A  2/1878 Fahnestock
321,847 A  7/1885 Peirce et al.
(Continued)

FOREIGN PATENT DOCUMENTS

CA  2505892  5/2004
JP  2008307281  12/2008
(Continued)

OTHER PUBLICATIONS

USPTO; Office Action dated Jan. 5, 2015 in U.S. Appl. No. 12/939,136.
(Continued)

*Primary Examiner* — Kandasamy Thangavelu
(74) *Attorney, Agent, or Firm* — Snell & Wilmer L.L.P.

(57) ABSTRACT

System and processes for optimal selection of teeth for dentures based on the anatomical measurements and bite impressions of the patient. This information is applied in an iterative manner to rules that balance the anatomical and aesthetic considerations to select the best teeth for a patient. The system may also use this information in an iterative manner to rules that balance the anatomical and aesthetic considerations to design the optimal denture base for the patient as well.

23 Claims, 6 Drawing Sheets

(51) Int. Cl.
*G06T 17/00* (2006.01)
*A61C 13/00* (2006.01)

(56) References Cited

U.S. PATENT DOCUMENTS

| | | | |
|---|---|---|---|
| 711,324 A | 10/1902 | Lacy | |
| 1,223,450 A | 4/1917 | Van Allen | |
| 1,293,627 A | 2/1919 | Bowers | |
| 1,585,348 A | 5/1926 | Hick et al. | |
| 1,652,910 A | 12/1927 | Psayla | |
| 1,714,185 A | 5/1929 | Hugh | |
| 1,863,591 A | 6/1932 | Crowell | |
| 1,914,606 A | 6/1933 | Kinna et al. | |
| 2,107,181 A | 2/1938 | Guyton | |
| 2,418,833 A | 4/1947 | Harris et al. | |
| 2,472,492 A | 6/1949 | Saffir | |
| 2,641,835 A | 6/1953 | Greenmun | |
| 2,985,961 A | 5/1961 | Schwartz | |
| 2,994,957 A | 8/1961 | Mcleod | |
| 3,083,459 A | 4/1963 | McMurry et al. | |
| 3,241,238 A | 3/1966 | Kertsten | |
| 3,644,996 A | 2/1972 | Weinkle | |
| 3,667,123 A | 6/1972 | Huey | |
| 3,727,309 A | 4/1973 | Huey | |
| 3,748,739 A | 7/1973 | Thibert | |
| 3,813,777 A | 6/1974 | Van Handel et al. | |
| 3,844,702 A | 10/1974 | Dimmer et al. | |
| 4,029,632 A | 6/1977 | Gross et al. | |
| 4,227,877 A | 10/1980 | Tureaud et al. | |
| 4,247,287 A | 1/1981 | Gigante | |
| 4,299,573 A | 11/1981 | Ricci | |
| 4,533,325 A | 8/1985 | Blair | |
| 4,591,341 A | 5/1986 | Andrews | |
| 4,634,377 A | 1/1987 | Behrend | |
| 4,784,608 A | 11/1988 | Mays | |
| 4,931,016 A | 6/1990 | Sillard | |
| 5,098,296 A | 3/1992 | Cullen | |
| 5,151,044 A | 9/1992 | Rotsaert | |
| 5,188,529 A | 2/1993 | Luth | |
| 5,427,906 A | 6/1995 | Hansen | |
| 5,672,305 A | 9/1997 | Kogure | |
| 5,711,668 A | 1/1998 | Huestis | |
| 5,716,214 A | 2/1998 | Lund | |
| 5,718,584 A | 2/1998 | Wong | |
| 5,833,461 A | 11/1998 | Wong | |
| 5,839,900 A | 11/1998 | Billet et al. | |
| 6,056,547 A | 5/2000 | Names | |
| 6,139,322 A | 10/2000 | Liu | |
| 6,149,427 A | 11/2000 | Van Handel | |
| 6,224,372 B1 | 5/2001 | Ibsen et al. | |
| 6,227,851 B1 | 5/2001 | Chishti | |
| 6,384,107 B2 | 5/2002 | Liu | |
| 6,422,864 B1 | 7/2002 | Glatt | |
| 6,488,503 B1 | 12/2002 | Lichkus et al. | |
| 6,616,444 B2 | 9/2003 | Andreiko et al. | |
| 6,851,949 B1 | 2/2005 | Sachdeva | |
| 7,021,934 B2 | 4/2006 | Aravena | |
| 7,153,135 B1 | 12/2006 | Thomas | |
| 7,234,940 B2 | 6/2007 | Weissman | |
| 7,433,810 B2 | 10/2008 | Pavloskaia et al. | |
| 7,474,932 B2 | 1/2009 | Geng | |
| 7,758,345 B1 | 7/2010 | Christensen | |
| 8,043,091 B2 | 10/2011 | Schmitt | |
| 8,348,669 B1 | 1/2013 | Schmitt | |
| 8,567,408 B2 | 10/2013 | Roettger | |
| 8,641,938 B2 | 2/2014 | Howe | |
| 8,801,431 B2 | 8/2014 | Thompson et al. | |
| 8,875,398 B2 | 11/2014 | Balshi et al. | |
| 9,055,993 B2 | 6/2015 | Grobbee et al. | |
| 2002/0015934 A1* | 2/2002 | Rubbert et al. | 433/29 |
| 2002/0180760 A1* | 12/2002 | Rubbert et al. | 345/630 |
| 2003/0108845 A1 | 6/2003 | Giovannone | |
| 2003/0162147 A1 | 8/2003 | Dequeker | |
| 2003/0163291 A1* | 8/2003 | Jordan et al. | 703/1 |
| 2003/0211444 A1 | 11/2003 | Andrews | |
| 2004/0005530 A1 | 1/2004 | Mullaly | |
| 2004/0029068 A1* | 2/2004 | Sachdeva et al. | 433/24 |
| 2004/0219490 A1 | 11/2004 | Gartner et al. | |
| 2005/0175957 A1 | 8/2005 | Haje | |
| 2005/0186539 A1 | 8/2005 | McLean et al. | |
| 2005/0284489 A1 | 12/2005 | Ambis | |
| 2006/0040232 A1 | 2/2006 | Shoup | |
| 2006/0040236 A1 | 2/2006 | Schmitt | |
| 2006/0063135 A1* | 3/2006 | Mehl | 433/223 |
| 2006/0210945 A1 | 9/2006 | Savic et al. | |
| 2006/0286507 A1 | 12/2006 | Dequeker | |
| 2007/0154868 A1* | 7/2007 | Scharlack et al. | 433/215 |
| 2007/0231774 A1 | 10/2007 | Massad | |
| 2008/0085489 A1 | 4/2008 | Schmitt | |
| 2008/0090207 A1 | 4/2008 | Rubbert | |
| 2008/0127698 A1 | 6/2008 | Luckey et al. | |
| 2008/0206710 A1* | 8/2008 | Kruth et al. | 433/174 |
| 2008/0206714 A1 | 8/2008 | Schmitt | |
| 2008/0209974 A1 | 9/2008 | Ewolski et al. | |
| 2008/0300716 A1 | 12/2008 | Kopelman | |
| 2009/0148813 A1 | 6/2009 | Sun et al. | |
| 2009/0162813 A1 | 6/2009 | Glor | |
| 2009/0287332 A1 | 11/2009 | Adusumilli et al. | |
| 2009/0291407 A1 | 11/2009 | Kuo | |
| 2009/0325125 A1 | 12/2009 | Diangelo et al. | |
| 2010/0015572 A1 | 1/2010 | Dirkes et al. | |
| 2010/0062394 A1 | 3/2010 | Jones et al. | |
| 2010/0086186 A1 | 4/2010 | Zug et al. | |
| 2010/0094446 A1 | 4/2010 | Baloch et al. | |
| 2010/0105011 A1* | 4/2010 | Karkar et al. | 433/215 |
| 2010/0324875 A1 | 12/2010 | Kalili | |
| 2011/0045442 A1 | 2/2011 | Adusumilli | |
| 2011/0112804 A1 | 5/2011 | Chishti et al. | |
| 2011/0129796 A1 | 6/2011 | Riggio | |
| 2011/0236856 A1* | 9/2011 | Kanazawa et al. | 433/199.1 |
| 2011/0244417 A1 | 10/2011 | Hilsen et al. | |
| 2012/0058449 A1 | 3/2012 | Sklarski et al. | |
| 2012/0095732 A1 | 4/2012 | Fisker et al. | |
| 2012/0100500 A1 | 4/2012 | Gao | |
| 2012/0178045 A1 | 7/2012 | Massad | |
| 2012/0179281 A1* | 7/2012 | Steingart et al. | 700/97 |
| 2012/0258426 A1 | 10/2012 | Boe | |
| 2012/0285019 A1 | 11/2012 | Schechner et al. | |
| 2012/0329008 A1 | 12/2012 | Fishman et al. | |
| 2013/0108988 A1 | 5/2013 | Simoncic | |
| 2013/0209962 A1 | 8/2013 | Thompson et al. | |
| 2013/0216978 A1 | 8/2013 | Thompson et al. | |
| 2013/0221554 A1* | 8/2013 | Jung et al. | 264/16 |
| 2013/0249132 A1 | 9/2013 | Thompson | |
| 2013/0280672 A1 | 10/2013 | Thompson | |
| 2013/0316302 A1 | 11/2013 | Fisker | |
| 2014/0045967 A1 | 2/2014 | Thomas et al. | |
| 2014/0272796 A1 | 9/2014 | Grobbee et al. | |
| 2015/0010885 A1 | 1/2015 | Balshi et al. | |
| 2015/0037760 A1 | 2/2015 | Thompson et al. | |
| 2015/0064653 A1 | 3/2015 | Grobbee et al. | |
| 2015/0134094 A1 | 5/2015 | Thompson et al. | |
| 2015/0230891 A1 | 8/2015 | Grobbee et al. | |
| 2015/0245891 A1 | 9/2015 | Grobbee | |
| 2015/0245892 A1 | 9/2015 | Grobbee | |

FOREIGN PATENT DOCUMENTS

| | | |
|---|---|---|
| WO | 2001032096 | 12/2001 |
| WO | 2009105661 | 8/2009 |
| WO | 2009105700 | 8/2009 |
| WO | 2010022479 | 3/2010 |
| WO | 2012041329 | 4/2012 |
| WO | 2012061652 | 5/2012 |
| WO | 2012061655 | 5/2012 |
| WO | 2012061659 | 5/2012 |
| WO | 2012061660 | 5/2012 |
| WO | 2014130536 | 8/2014 |
| WO | 2015031062 | 3/2015 |

OTHER PUBLICATIONS

USPTO; Restriction Requirement dated Feb. 12, 2015 in U.S. Appl. No. 13/369,238.

(56) References Cited

OTHER PUBLICATIONS

USPTO; Advisory Action dated Feb. 23, 2015 in U.S. Appl. No. 13/830,963.
USPTO; Non-Final Office Action dated Dec. 19, 2014 in U.S. Appl. No. 14/013,295.
PCT; International Search Report and Written Opinion dated Jul. 18, 2012 in Application No. PCT/US2011/059230.
PCT; International Preliminary Report on Patentability dated May 8, 2013 in Application No. PCT/US2011/059230.
PCT; International Search Report and Written Opinion dated Jul. 18, 2012 in Application No. PCT/US2011/059235.
PCT; International Preliminary Report on Patentability dated May 8, 2013 in Application No. PCT/US2011/059235.
PCT; International Search Report and Written Opinion dated Jul. 9, 2012 in Application No. PCT/US2011/059239.
PCT; International Preliminary Report on Patentability dated May 8, 2013 in Application No. PCT/US2011/059239.
PCT; International Search Report and Written Opinion dated Jul. 18, 2012 in Application No. PCT/US2011/059240.
PCT; International Preliminary Report on Patentability dated May 8, 2013 in Application No. PCT/US2011/059240.
USPTO; Final Office Action dated Mar. 6, 2014 in U.S. Appl. No. 13/249,210.
USPTO; Restriction Requirement dated Dec. 23, 2013 in U.S. Appl. No. 13/823,466.
EPO; European Search Report dated Mar. 4, 2014 in Application No. 11838839.6.
USPTO; Non-Final Office Action dated Apr. 9, 2015 in U.S. Appl. No. 12/939,138.
USPTO; Final Office Action dated Mar. 26, 2015 in U.S. Appl. No. 13/823,466.
USPTO; Notice of Allowance dated Jun. 22, 2015 in U.S. Appl. No. 13/823,621.
USPTO; Notice of Allowance dated Apr. 13, 2015 in U.S. Appl. No. 14/013,295.
USPTO; Notice of Allowance dated Jun. 6, 2014 in U.S. Appl. No. 13/249,210.
USPTO; Non-Final Office Action dated Jun. 6, 2014 in U.S. Appl. No. 13/823,466.
USPTO; Non-Final Office Action dated Jun. 20, 2014 in U.S. Appl. No. 13/830,963.
USPTO; Restriction Requirement dated Jul. 2, 2014 in U.S. Appl. No. 14/195,348.
EPO; European Search Report and Opinion dated Mar. 3, 2014 in Application No. 11838843.8.
USPTO; Office Action dated Sep. 24, 2013 in U.S. Appl. No. 13/249,210.
USPTO; Non-Final Office Action dated Oct. 23, 2014 in U.S. Appl. No. 13/823,621.
USPTO; Final Office Action dated dated Nov. 7, 2014 in U.S. Appl. No. 13/830,963.
USPTO; Restriction Requirement dated Sep. 5, 2014 in U.S. Appl. No. 13/823,621.
USPTO; Office Action dated Aug. 21, 2014 in U.S. Appl. No. 14/195,348.
USPTO; Final Office Action dated Oct. 21, 2014 in U.S. Appl. No. 14/195,348.
PCT; International Search Report and Written Opinion dated Aug. 7, 2014 in Application No. PCT/US2014/023654.
PCT; International Search Report and Written Opinion dated Jul. 25, 2014 in Application No. PCT/US2014/017136.
USPTO; Final Office Action dated Sep. 25, 2015 in U.S. Appl. No. 12/939,136.
USPTO; Final Office Action dated Aug. 19, 2015 in U.S. Appl. No. 12/939,138.
USPTO; Non-Final Office Action dated Sep. 21, 2015 in U.S. Appl. No. 13/369,238.
USPTO; Notice of Allowance dated Aug. 24, 2015 in U.S. Appl. No. 13/823,662.
USPTO; Non-Final Office Action dated Aug. 13, 2015 in U.S. Appl. No. 13/830,963.
USPTO; Non-Final Office Action dated Aug. 11, 2015 in U.S. Appl. No. 14/195,348.

* cited by examiner

SYSTEM AND PROCESS FOR OPTIMIZATION OF DENTURES

RELATED APPLICATIONS

This application is a U.S. National Phase filing under 35 U.S.C. §371 of PCT/US2011/059235, filed on Nov. 3, 2011, which claims priority to U.S. Non-Provisional application Ser. No. 13/939,141 filed on Nov. 3, 2010.

FIELD OF THE INVENTION

This invention relates to the field of the manufacture of dentures, and particularly to the optimization of denture bases and teeth.

BACKGROUND OF THE INVENTION

Dentures have long been used by patients for a variety of reasons. Modern dentures are relatively comfortable and not easily detectable. The process of being properly fitted for dentures typically requires numerous fittings and skill of the dentist. The typical process for being fitted for dentures requires a first trip by the patient for primary impressions to be made. A plaster model is formed from the primary impressions from which a custom tray is fabricated.

The patient then makes another trip to the dentist where a final impression using the custom tray is made. A working model in stone is fabricated from the final impression. A wax rim formed from the working model and provided to the dentist.

The patient makes a third trip to the dentist where the wax rims are marked up with data points, measurements, shades, etc. The marked up rims are mounted on an articulator to set the bite alignment and vertical spacing of the dentures. Teeth are selected from a library.

The selection and placement of the teeth is relatively subjective. Generally, the dentist or lab technician will select the teeth in accordance with a classification system that groups teeth into square, tapering, ovoid or combinations of each and relates them to facial outline. One example of such a system is known as the Williams Classification, and is derived from a theory that an inverted maxillary incisor tooth has the same general shape as the person's face. Different dentists or lab technicians will make different choices as to the choice of the tooth shape. Similarly, the shading of the teeth is also relatively subjective as well. The placement of the teeth in the denture base is also a subjective test, dependent upon the skill and experience of the technician. Normally, the lab technician will not have access to the patient or their history for determining the appropriate teeth and placement.

The teeth are set up in the wax rim. Occlusions are identified and the teeth are ground if necessary. The denture base with the full aesthetic wax up is delivered to the dentist.

The patient makes a fourth trip to the dentist for a try-in of the wax-up. The dentist looks at the bite, the speech, the shade, teeth position and the occlusions of the patient while the patient uses various jaw movements. If the dentist identifies any problems, the wax-up is sent back to the lab for additional changes. This process is repeated until the dentist and patient are satisfied.

Once the wax-up has been accepted, it is sent to the lab where a final wax-up is created. The borders are sealed out and the post dam is cased. A denture base is then created, usually by a flask molding process of investing the cast and the wax-up in a flask to make a mold that is used to form the denture base. The mold is then cured and divested from the flask. The denture is then processed by once again articulating the denture to check the bite. The denture is then analyzed and if passed, then undergoes a bulk trim. The denture then undergoes a final finish and polish. If the denture passes quality inspection it is sent to the dentist. The patient comes in for a fifth visit for a final try-in and delivery.

This process is time-consuming, requires multiple visits by the patient and multiple transmissions of data and models between the dental lab and dentist. The previous systems also require considerable skills of the dentist and the dental lab technicians. Additionally, each step along the process can lead to introduction of errors that must later be corrected.

SUMMARY OF THE INVENTION

The present invention provides a system that will quickly provide an optimal denture for the patient with a limited number of visits required of the patient to the dentist. The system utilizes an iterative process that will optimize the selection of the teeth for a particular patient as well as optimizing the denture base for the selected teeth. This optimization process for the teeth and the denture base is based on the application of rules regarding the anatomical features of a particular patient as measured by the dentists and from a scan of the bite impressions of that patient. The iterative application of these rules to those measured values of the anatomical features of the patient optimize the denture base. Once the optimal denture base has been designed, the denture teeth are selected from a library or fabricated to best fit the denture base.

The terms denture base generally refers to the part of a denture that fits the oral mucosa of the basal seat, restores the normal contours of the soft tissues of the edentulous or partly edentulous mouth, and supports the artificial teeth. The term denture refers to the denture base with the artificial teeth attached. The term anatomical landmarks refers to the structures on the anatomy of the wearer that define the periphery of the denture. The term anatomical features includes the features corresponding to the anatomical landmarks of the wearer as well as functional and aesthetics features that are created in the denture.

A preferred embodiment of the present invention provides a system that implements a series of rules concerning the optimal selection or design, and placement of teeth in a denture base. The rules are applied in an iterative process to determine the best teeth for the patient. Measurements of key anatomical features and functional of the patient's face provide values that are applied to the rules for the determination. Scans of the bite alignment impressions are also used for these determinations. Aesthetic as well as functional considerations enter into the determination of the best teeth for the patient.

In another preferred embodiment, the system creates a digital record of the best teeth for the patient as described above. The teeth are then fabricated through rapid fabrication processes either individually or directly onto the denture base.

Another preferred embodiment of the present invention also determines adjustments for the denture base design for the best fit of a denture in regard to the anatomical and aesthetic features of a patient. These rules compare various values to determine the best vertical height of the denture base, the best thicknesses of the arch, the best occlusions for the selected teeth to determine the optimal denture base as well as other parameters. This information regarding the denture base is then used to manufacture a denture base to produce this denture base.

The information regarding the anatomical and aesthetic features of a patient is derived from measurements taken by the dentist. These measurements include such anatomical measurements regarding the vertical height relative to the upper and lowerbite alignment; the lip support; lip mid line, smile line and centric relationship between the jaws. Scan of the bite impressions are also provided as well. These measurements can be taken with individual tools, or in one preferred embodiment, a single tool is able to provide all of these measurements. This information is then transmitted to the system for use in designing or selecting the optimal teeth and/or the optimal denture base.

One preferred embodiment also produces a rendition of a three dimensional model of the patient, the optimal denture base along with the selected teeth that can be transmitted to the dentist. The dentist can then adjust the information on the measurements of the patient to create changes in the optimal denture base that is derived from the observations of the three dimensional model. These changes can be based on aesthetic features or can also include functional/anatomical changes as well.

In a preferred embodiment, a three dimensional model of the patient, the denture base and selected teeth is rendered from the measurements and the scans of the bite impressions. This model can be used to optimize the occlusal planes of the teeth and articulation of the patient's dentures. Finite element analysis may also be used to determine the optimal design of the denture base and the joining of the teeth and base.

These and other features of the present invention will be evident from the ensuing detailed description of preferred embodiments, from the drawings and from the claims.

DETAILED DESCRIPTIONS OF PREFERRED EMBODIMENTS

The present invention provides systems and process for optimizing the fabrication of denture bases. Descriptive embodiments are provided below for explanatory purposes. It is to be expressly understood that the present invention is not be limited to these descriptive embodiments. Other embodiments are considered to be within the scope of the present invention, including without limitation the use of the present invention for other applications, such as denture duplication, dental implants, and other dental applications. The descriptions below discuss the systems of the present invention as used in dental labs, but it is to be expressly understood that these systems could also be implemented in the dentist office or through a network allowing interaction between the dentist and the dental lab through the systems. The processes and systems of the present invention may also be used in combination with all or parts of the following applications filed on Nov. 3, 2010, entitled System and Processes for Forming Anatomical Features in Dentures, Ser. No. 12/939,138; System and Process for Duplication of Dentures, Ser. No. 12/939,136; Combination Tool for Anatomical Measurement for Denture Manufacture, Ser. No. 61/409,914; and Removable Handle for Use with Dentures, Ser. No. 12/939,143; all of which are hereby incorporated herein by reference.

Overview

The system of a preferred embodiment uses a process whereby the dentist obtains a scan of the patient's bite impressions and a number of measurements from the patient on their initial visit. These measurements are based on the anatomical features of the patient. The dentist may also provide information regarding to the selection of the teeth. This information is transmitted to the dental lab where the system creates a digital three dimensional model of the denture base from the scans and from the measurements. It is to be expressly understood that a three dimensional model of the patient's jaw structure may also be created. Additionally, it is to be expressly understood that these digital models could also be created from other information, such as an intraoral scan or CT scan.

This model is then optimized to select the "best" teeth for the patient. Also, the process may optimize the denture base for use with the teeth for the best fit for the patient. This optimization process applies a series of rules to come up with the "perfect" denture for the patient. The best fit for the patient means anatomical, bone shape, bone quality, functional and aesthetics. For purposes of the present invention, anatomy includes, vertical height, lip support, height of ridge, frenums, bone density, bone quality and bone shape from a CT scan.

A digital three dimensional model of the denture base along with the selected teeth fitted on the patient is sent to the dentist for a virtual try-in. The dentist may be allowed to make aesthetic changes on the model, such as the shading of the teeth, the smile line of the patient, or other aesthetic changes. The approved model is then transmitted back to the lab. A denture base and teeth are then created from the three dimensional model, either through traditional denture fabrication processes or directly by milling or rapid prototyping processes. The teeth are temporarily installed and the temporary denture is sent to the dentists for a patient try-in. If the dentist and patient are not satisfied, the denture is used as a secondary impression try and an impression is taken and scanned. The denture model is tweaked, a new denture base is fabricated and teeth are temporarily installed for another patient try-in. Once the denture has been accepted by the dentist and patient, the teeth are permanently installed and the final trim and polish takes place. The denture is then ready for final patient installation.

Measurement Process

Figure 2:
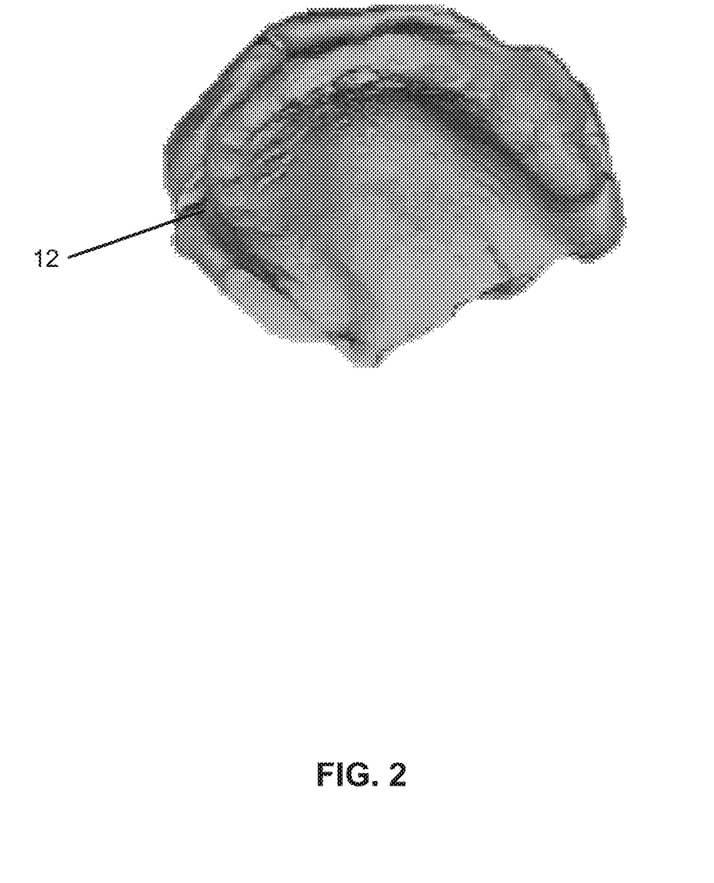
FIG. 2 is an illustration of the upper impressions.
Figure 3:
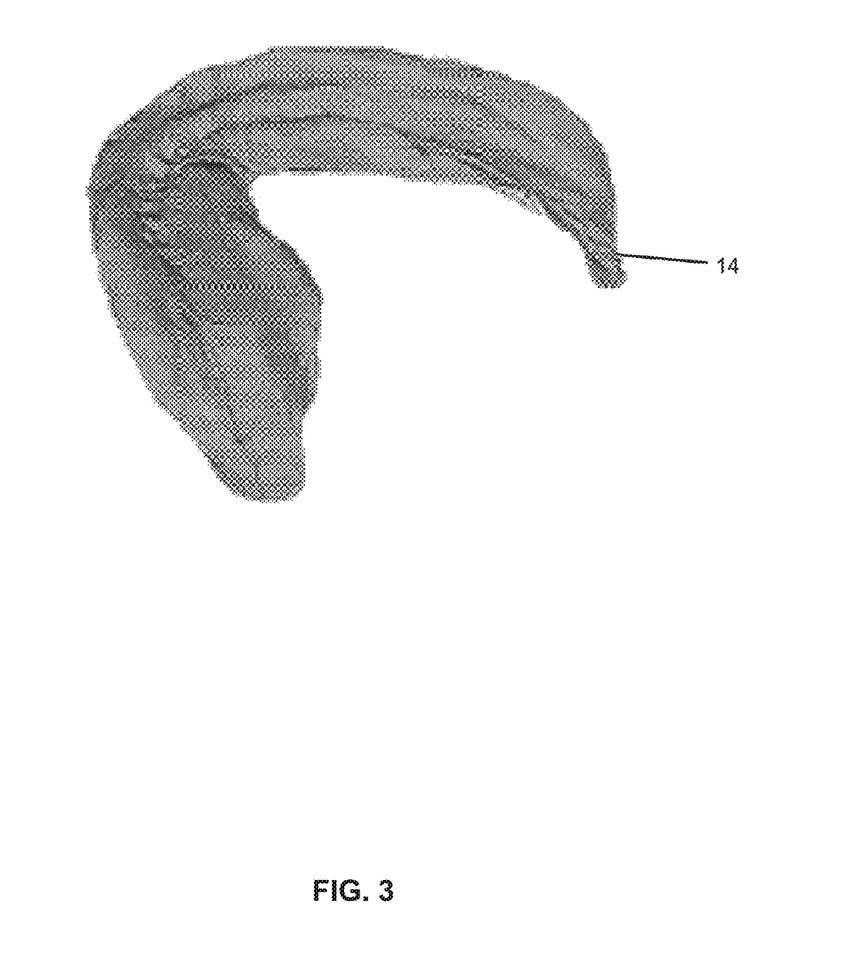
FIG. 3 is an illustration of the lower impression of a digital three dimension model of the digital model with teeth

The dentist obtains data regarding several anatomical features of the patient to send to the dental lab. First, the dentist obtains scans of the bite impressions. This can be done by using an upper bite impression tray, a lower bite impression tray or a triple bite impression tray that simultaneously takes both upper and lower bite impressions. Bite impressions provide the bite registration, the prepared area and the opposing teeth. The surface of the upper and lower bite impressions 12, 14 are digitally scanned as shown in FIGS. 2 and 3 and transmitted to the lab or directly into the system. Alternatively, or in conjunction with this process, an intraoral digital scanning or other scanning techniques may be done.

The dentist also takes additional measurements of anatomical features of the patient. These include, without limitation, the vertical height relation to the upper and lower bite alignment; the lip support of the patient; the smile line of the patient; the centric relationship of the patient; and the midline measurement. Other measurements may be taken as well.

The lip line measurement is intended to provide a measurement of the upper lip from the anterior papilla at rest. This is traditionally measured by a papillameter which consist of a vestibule shield, incisive papilla rest and an vertical handle with measurement increments.

The smile line measurement can also be determined by the papillameter. The device is inserted into position and the patient is requested to smile so that the lip line at that position from the anterior papilla can be measured.

The midline is determined from typically from the existing intraoral anatomic structures, usually the maxillary anterior (labial) frenum.

The vertical height dimension is typically determined from measurements taken from nose and chin reference points. Measurements of the vertical height are taken at rest and of the vertical dimension of occlusion.

A centric tray is commonly used to take a double arch registration to record vertical and centric jaw registration.

The occlusal plane is an orientation of the position of an imaginary occlusal plane which theoretically touches the incisal edges of the incisors and tips of the occluding surface of the posterior teeth. A normal occlusal plane extends parallel to a line drawn from the tragus of the ear to the ala of the nose and parallel to the interpupillary line (Camper's Line). This ensures that the patient will not dislodge the lower denture, particularly while eating and not bite the lateral borders of the tongue. Tools for measuring the occlusal plane typically include a thin flat plane have a curved bite piece and a pair of laterally and distally extending wings projecting from the bite piece.

There are individual tools for each of these measurements. A single tool for obtaining all of these measurements is disclosed in Combination Tool for Anatomical Measurement for Denture Manufacture, Ser. No. 61/409,914 and is incorporated by reference. In a preferred embodiment of the present invention, this tool is used to supply the necessary measurements for the optimization process for designing a denture.

The dentist also selects the teeth to be fitted into the denture base. Typically, the dentist will use a facial meter, anterior tooth selection guide and a library catalog to determine the appropriate teeth. Other methods may be used as well along with the determination of the appropriate shading of the teeth.

The scan, measurements and teeth selection are then transmitted to the dental lab or directly into the system.

Optimization Process

The system of a preferred embodiment then creates a digital three dimensional model of the patient's jaw structure, arches, gums, etc. based on the scan and on the measurements. Systems for creating such digital three dimensional models are disclosed in U.S. Pat. No. 6,616,444, assigned to Ormco Corporation and patents relating to that patent, U.S. Pat. No. 6,851,949, assigned to OraMetrix, Inc. and patents relating to that patent; and U.S. Pat. No. 7,433,810, assigned to Align Technology, Inc. and patents relating to that patent, all of the above cited patents and patents and published patent applications relating to them are incorporated herein by reference. These systems are disclosed for use with orthodontic appliances. The present invention takes information from these systems and including the additional information described above in regard to the measurements of the patient's anatomy to create a digital model 12 and 14 as shown in FIGS. 2 and 3 for use with creating and optimizing a denture.

Figure 4:
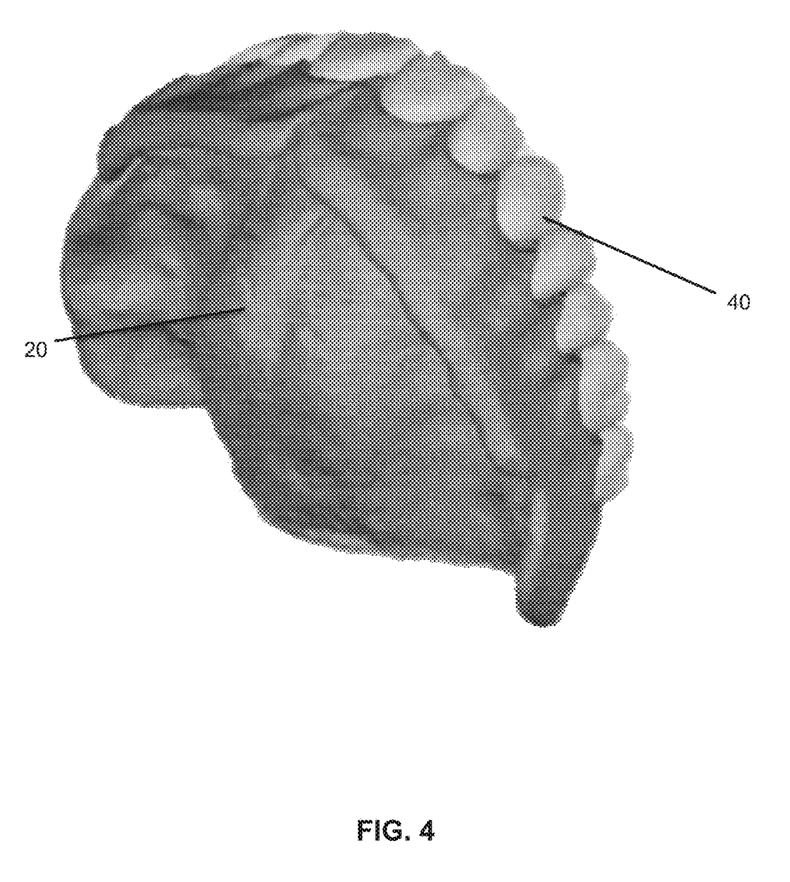
FIG. 4 is an illustration of the optimal denture base and teeth.
Figure 5:
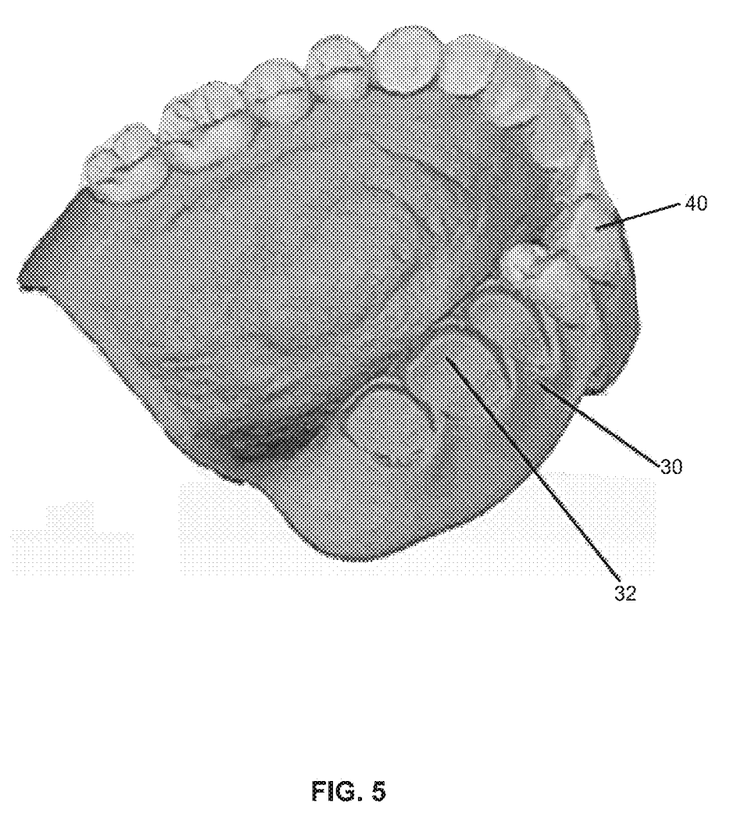
FIG. 5 is an illustration of another view of the optimal denture base and teeth.
Figure 6:
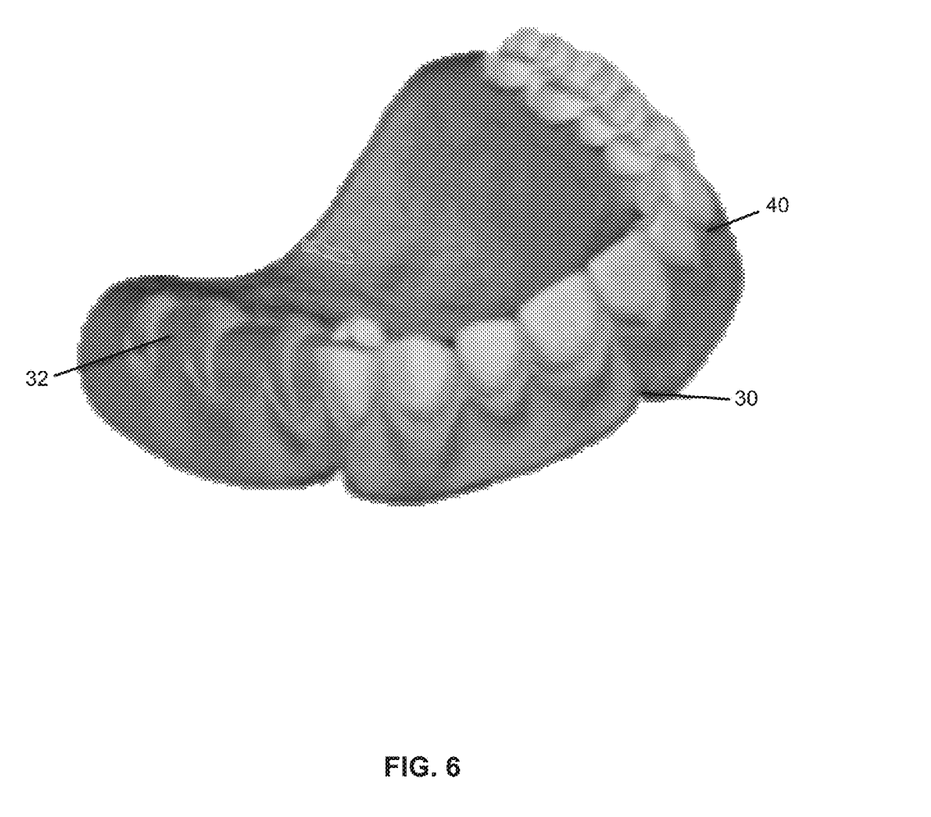
FIG. 6 is an illustration of a further view of the optimal denture base and teeth.

Once a digital model has been created, the system applies iterative rules to determine the "perfect" teeth 40 as shown in FIGS. 4 and 5 for the patient as well as optimize the denture base 20 as shown in FIG. 4 for use with the patient and teeth These rules take into consideration the size and shape of the teeth, such as square, round, ovoid, the shadings of the teeth, the smile line, the lip support, occlusal plane, and other aesthetic considerations as well as functional considerations such as occlusions, arch length, depth and height and other features. These factors are used to develop the rules for the system and process. The data values from the measurements and from the impression scans are then applied to the rules through iterations to select the best teeth every time. The previous subjective selection by lab technicians is eliminated and the best teeth are selected every time. The teeth, such as teeth 40 are then installed in tooth pockets 32 of denture base 30, as shown in FIGS. 4, 5 and 6.

The system may also take into consideration the earlier dental records of the patient. These dental records may be used to design dentures that restore the patient to their dentition of earlier years, to recreate their smile and facial features. The teeth records from earlier visits may be used to design or select the new teeth.

The system may also be able to design and fabricate teeth based on the digital optimization, rather than to select from a preexisting library of teeth. Rapid prototyping, machining, or other equipment can be used to fabricate the teeth with or without the denture base. In particular, one preferred embodiment uses rapid prototyping equipment capable of using multiple materials to fabricate an acrylic denture base with porcelain teeth or a multi-color in acrylic, although other materials may be used as well.

The system may also further optimize the denture base as well to ensure the best balance between aesthetics and functionality based on the individual anatomical features of the patient. Rules are developed that take into consideration such factors as the arch length, the arch depth and arch height, particularly when the teeth have been selected. Other factors, such as occlusions, vertical height, strength may also be used to determine the optimal base. Also, anatomical considerations such as bone quality, bone shape and bone density are considered.

Figure 1:
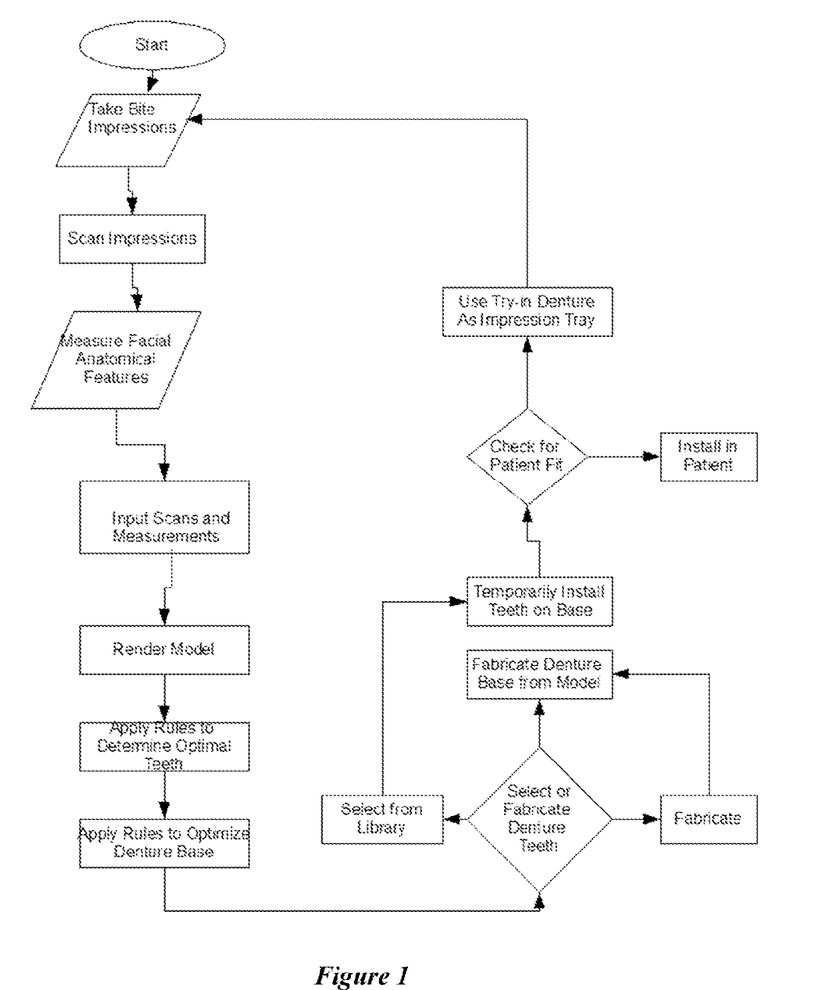
FIG. 1 illustrates a work flow of the optimization of the design of the denture base.

These rules are used to balance the anatomical fit of the denture base such as the arch height vs. the thickness of the palate vs. the height of the teeth vs. the occlusions of the teeth and so on. The rules may be weighted to give greater bias for certain rules as compared to others. The rules may also include aesthetic considerations as well, such as the smile line, the lip support, etc. The system then iteratively applies the rules to create the best balance between the anatomical and aesthetic consideration to optimize the denture base. A work flow diagram is shown in FIG. 1 that describes this process.

The system may also apply other functionality parameters to design the optimal denture for a patient. For example, the system may apply a finite analysis to the denture base and the teeth to determine the strength of the denture at different locations. This will enable the denture to be adjusted by the use of different materials, different joining compounds, different thicknesses at selected locations and other considerations.

A digital three dimensional model of the patient with the denture base and teeth is then provided to the dentist in one embodiment of the present invention. The dentist can then inspect the aesthetic features of the denture fitted in the patient. The dentist may inspect the smile line, the lip lines, teeth selection, teeth shadings and other aesthetic features. In one embodiment, the dentist is given the ability to make adjustments on the model to determine the ideal aesthetics for the patient. In another embodiment, the dentist is also given the ability to make adjustments on certain of the functional anatomical features as well, such as the arch height or occlusions. Once the dentist is satisfied with the optimized denture, any changes are sent back to the lab.

The system can then select the denture base that best fits the optimized digital model from a library of denture teeth. Alternatively, the denture teeth is directly fabricated using rapid prototyping techniques such as layer manufacturing, machined or milled. The denture base is then fabricated and the teeth are temporarily installed. The temporary denture is then shipped to the dentist for a patient try-in. If the fit is not satisfactory, then the denture is used as a secondary impression tray and new impressions are created and scanned. This scan along with any additional changes in measurement data is put back into the system. The system then once again performs an iterative process using the rules to determine a model that is the best fit for that patient. The denture base is then fabricated. The teeth are once again temporarily installed and the denture is ready for another try-in with the patient.

This process is continued until the patient and dentist are satisfied with the denture. Once the denture has been deemed satisfactory, the teeth can be permanently installed and the final finish and polish procedures are performed. The finished denture is then shipped to the dentist for the patient final try-in and acceptance.

It is to be expressly understood that the above description is intended only for explanatory purposes and is not meant to limit the scope of the claimed inventions. Other embodiments are considered to be within the scope of the claimed inventions.

What is claimed is:

1. A computer-implemented method for determining a best denture for a patient, the method comprising:
   determining measurements of anatomical features of a patient;
   scanning impression of bite alignments of the patient;
   designing a denture base that best fits the patient;
   applying a plurality of rules to the measurements and scanned impression in an iterative fashion to select the teeth that will best fit the patient.

2. The method of claim 1 wherein said step of selecting teeth includes:
   selecting teeth from a library of teeth.

3. The method of claim 1 wherein said step of selecting teeth includes:
   directly manufacturing teeth from the information produced from the selected teeth.

4. The method of claim 1 wherein said step of determining measurements of anatomical features of a patient includes:
   determining the measurements of at least one of the following group of anatomical features: lip support, smile line, lip height, vertical height, centric jaw relationships, bone quality, bone shape and bone density.

5. The method of claim 1 wherein said step of applying a plurality of rules to the measurements and scanned impression include:
   performing an iteration of rules concerning bone quality, aesthetics and functional relationships.

6. The method of claim 1 wherein said method further includes:
   providing a digital model of the denture base with the selected teeth on the patient for review by the originating dentist.

7. The method of claim 1 wherein said step of designing a denture base includes:
   applying the plurality of rules to the measurements and scanned impression in an iterative fashion to determine an optimal denture base that will best fit the patient.

8. The method of claim 7 wherein said method further includes the steps of:
   providing a digital model of the optimal denture base with the selected teeth on the patient for review by an originating dentist;
   providing a mechanism for allowing the dentist to make adjustments to the denture base model for aesthetic purposes.

9. The method of claim 1 wherein said method further includes the steps of:
   providing a digital model of the denture base with the selected teeth on the patient for review by an originating dentist; and
   providing a mechanism for allowing the dentist to make adjustments to the denture base model.

10. The method of claim 1 wherein the step of determining measurements of anatomical features of a patient further includes:
    using a single tool to take all of the measurements of the anatomical features.

11. A computer-implemented method for determining a best denture for a patient, the method comprising:
    determining measurements of anatomical features of a patient;
    scanning impressions of bite alignments of the patient;
    applying a plurality of rules to the measurements and scanned impressions in an iterative fashion to determine an optimal denture base for the patient; and
    applying the plurality of rules to the measurements and scanned impressions in an iterative fashion to select the teeth that will best fit the patient.

12. The method of claim 11, wherein the method further includes:
    temporarily installing the selected teeth to the denture base;
    allowing the patient to try the denture base and teeth;
    using the denture base as a secondary impression tray if the denture base did not properly fit and repeating the earlier steps to create a new optimal denture base for the patient to try;
    permanently installing the teeth if the denture base properly fits the patient; and
    providing a final denture base and teeth to the patient.

13. The method of claim 11 wherein said step of determining measurements of anatomical features of a patient includes:
    determining the measurements of at least one of the following group: lip support, smile line, arch height, vertical height, centric jaw relationships, bone quality, bone shape and bone density.

14. The method of claim 11 wherein said method further includes the step of:
    providing a digital model of the optimal denture base with the selected teeth on the patient for review by an originating dentist.

15. The method of claim 14 wherein said method further includes:
    fabricating the denture base from the information of the digital model.

16. The method of claim 14 wherein said method further includes:
    fabricating the denture base and select, or designed and manufactured teeth from the digital model.

17. The method of claim 11 wherein said method further includes the steps of:

providing a digital model of the optimal denture base with the selected teeth on the patient for review by an originating dentist;

providing a mechanism for allowing the dentist to make adjustments to the denture base model.

18. The method of claim 11 wherein said method further includes:

designing denture teeth using the rules.

19. A system for determining the best denture for a patient, the system comprising:

a processing device configured to execute computer-executable code;

a memory device connected to said processing device for storing computer-executable code;

an interface for receiving data relevant to a particular patient and storing said data in said memory device;

a rule editor for configuring rules for selecting, qualifying and designing the optimal teeth that will best fit a patient;

a rules engine for applying each of said configured rules to said data for a particular patient in an iterative scheme until the optimal teeth have been designed for that particular patient; and a selection engine for selecting teeth based on the design of the optimal teeth.

20. The system of claim 19 wherein said selection engine includes:

a library of teeth from which the teeth may be selected.

21. The system of claim 19 wherein said selection engine includes:

an interface to produce information from which the teeth may be directly manufactured.

22. The system of claim 19 wherein said system further includes:

a rule editor for configuring rules for selecting, qualifying and adapting the dimensions of an optimal denture base that will best fit a patient;

a rules engine for applying each of said configured rules to said data for a particular patient in an iterative scheme until the optimal denture base has been designed for that particular patient.

23. The system of claim 22 wherein said system further includes:

a rendering engine for creating a digital three dimensional model based on the information regarding a particular patient and from the optimal denture base and selected teeth;

an interface for transmitting said digital three dimensional model for display to another entity; and a tool engine for allowing the entity to make changes to the information regarding the particular patient based on said digital three dimensional model.

* * * * *